United States Patent [19]

Zinnes et al.

[11] 3,962,261
[45] June 8, 1976

[54] 2,3,4,5-TETRAHYDRO-5-OXO-1-BENZOTHIEPIN-4-CARBOXAMIDE 1,1-DIOXIDES

[75] Inventors: Harold Zinnes, Rockaway; Jagadish C. Sircar, Dover, both of N.J.

[73] Assignee: Warner-Lambert Company, Morris Plains, N.J.

[22] Filed: Aug. 6, 1975

[21] Appl. No.: 602,155

Related U.S. Application Data

[63] Continuation of Ser. No. 439,502, Feb. 4, 1974, abandoned.

[52] U.S. Cl. ............... 260/294.8 C; 260/306.8 R; 260/307 H; 260/327 B; 424/263; 424/270; 424/272; 424/275
[51] Int. Cl.² .......................... C07D 213/34
[58] Field of Search .............. 260/294.8 C, 327 B, 260/306.8 R, 307 H

[56] References Cited
UNITED STATES PATENTS

| | | | |
|---|---|---|---|
| 3,826,791 | 7/1974 | Zinnes et al. | 260/294.8 C |
| 3,828,055 | 8/1974 | Zinnes et al. | 260/294.8 C |

Primary Examiner—Alan L. Rotman
Attorney, Agent, or Firm—Albert H. Graddis; Frank S. Chow

[57] ABSTRACT

Compounds of the formula:

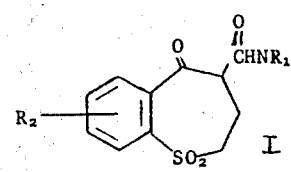

are disclosed. In the above formula, $R_1$ is aryl such as benzene or a heterocycle such as pyridine, isoxazole, or thiazole. The aryl or heterocyclic group $R_1$ is substituted or unsubstituted. $R_2$ is hydrogen, lower alkyl, halogen, lower alkoxy, trifluoromethyl and the like.

These compounds are useful as anti-inflammatory agents indicated in conditions such as rheumatoid arthritis.

4 Claims, No Drawings

2,3,4,5-TETRA HYDRO-5-OXO-1-BENZOTHIEPIN-4-CARBOXAMIDE 1,1-DIOXIDES

This is a continuation of application Ser. No. 439,502 filed Feb. 4, 1974, now abandoned.

The present invention relates to 2,3,4,5-tetrahydro-5-oxo-1-benzothiepin-4-carboxamide 1,1-dioxides having the following structural formula:

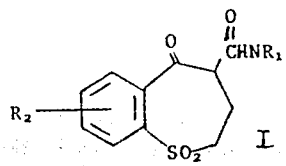

wherein $R_1$ is aryl or heterocyclic and $R_2$ is hydrogen, lower alkyl, halogen, alkoxy, trifluoromethyl and the like.

In the above definitions, "aryl" means a monocyclic aromatic hydrocarbon preferably of 6–10 carbon atoms such as, for example, phenyl, tolyl and the like. The term "heterocyclic" encompasses the monocyclic 5- and 6-membered heterocyclic rings having at least one hetero atom in the ring which may be nitrogen, oxygen or sulfur. Preferred heterocyclic radicals falling within this definition are pyridyl, isoxazole and thiazole.

Aryl or heterocyclic may be further substituted by groups such as lower alkyl, lower alkoxy, halo, and the like.

These compounds form salts with alkali metals such as sodium and potassium and these salts are also included within the scope of this invention.

The present invention also includes within its scope novel processes for the preparation of the above described compounds.

The compounds of this invention exhibit anti-inflammatory activity. Thus, for example, when administered orally or intraperitoneally to laboratory animals such as rats at a dose of 100 mg/kg they reduce the swelling in their paws which was previously induced by the injection of an irritant such as carrageenin.

The compounds of this invention are useful in the management of inflammatory conditions such as rheumatoid arthritis. Generally speaking, a dose of 100 mg/kg orally or by injection is recommended to provide relief. This dose may be repeated two or three times daily. Such a dose regimen can be varied depending upon the severity and the condition of the patient being treated.

In order to use these compounds they are formulated as an aqueous suspension utilizing known suspending agents such as gum tragacanth, methylcellulose and the like to form the desired suspension. Alternatively, the corresponding alkali metal salts are dissolved in water to form an aqueous solution.

According to one process of the invention, a ketone of structure II is treated with a secondary amine such as pyrrolidine to give an enamine of structure III. This is reacted with phosgene in the presence of a base such as triethylamine to give an acid chloride of structure IV. This is not isolated as such but is reacted directly with an aromatic or heterocyclic amine of formula $R_1NH_2$ to give an enamine amide of structure V. The latter are hydrolyzed with dilute acid to give the title compounds of structure I. The enamine amides of structure V are either isolated and purified or are hydrolyzed directly without prior purification.

This process is illustrated by the following reaction scheme:

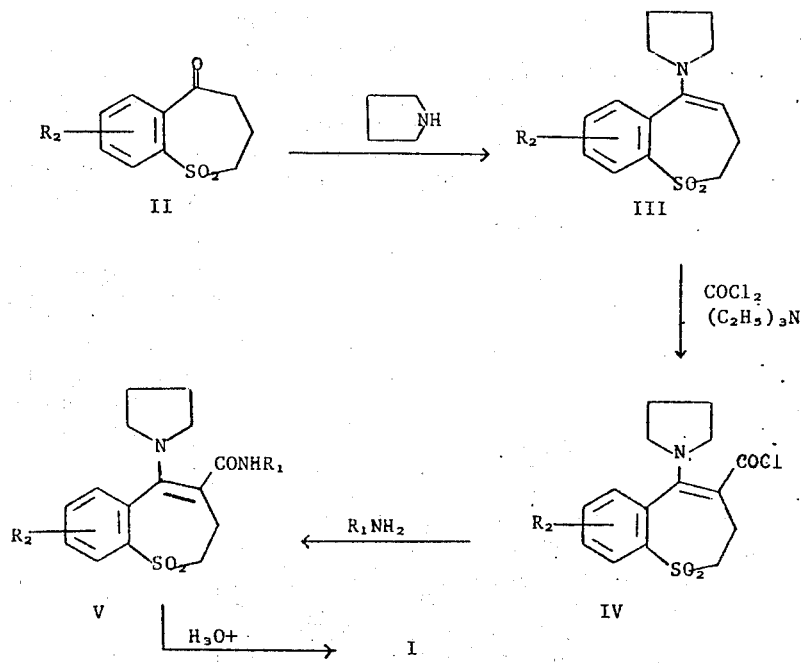

A second process of this invention involves treatment of the ketone II with a dialkyl carbonate and sodium hydride to form a keto ester of structure VI. This is refluxed with $R_1NH_2$ to give compound I.

This process is illustrated as follows:

II $\xrightarrow[(R_3O)_2CO]{NaH}$ 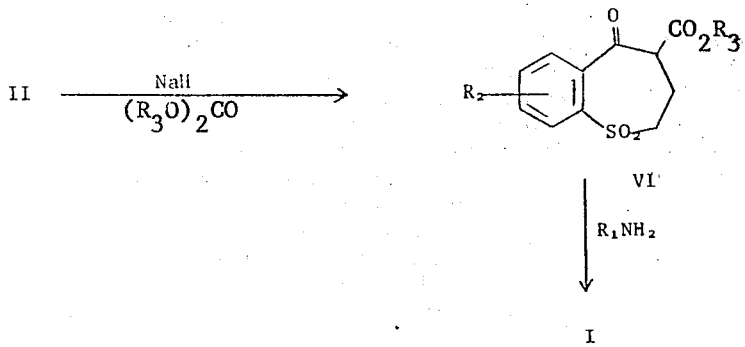

↓ $R_1NH_2$

I in which $R_3$ is lower alkyl.

The starting ketones II are prepared as described by V. J. Traynelis and R. F. Love, J.O.C. 26 2728 (1961).

To further illustrate the practice of this invention, the following examples are included:

EXAMPLE 1

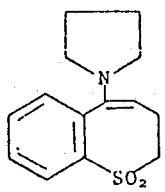

2,3-Dihydro-5-(1-pyrrolidinyl)-1-benzothiepin 1,1-Dioxide

A solution of 20.6 g (0.1 mol) of 3,4-dihydro-1-benzothiepin-5(2H)-one 1,1-dioxide, 9.6 g of pyrrolidine and 250 mg of p-toluenesulfonic acid in 250 ml of benzene was refluxed under a nitrogen atmosphere for 20 hours, using a Dean-Stark apparatus to remove the water which formed. Removal of the solvent under reduced pressure gave 27 g of a viscous oil which was used without further purification. The infrared spectrum showed the absence of a ketone band and the presence of a strong enamine band at 1620 cm$^{-1}$.

EXAMPLE 2

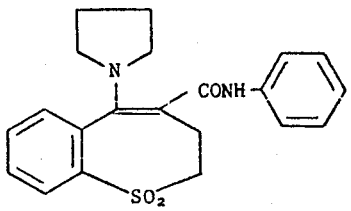

2,3-Dihydro-5-(1-pyrrolidinyl)-1-benzothiepin-4-carboxanilide 1,1-Dioxide

A mixture of 80 ml (contg 0.084 mol of COCl$_2$) of a 12.5% solution of phosgene in benzene and 80 ml of tetrahydrofuran was cooled to −50° and a solution of 22.0 g (0.08 mol) of crude 2,3-dihydro-5-(1-pyrrolidinyl)-1-benzothiepin 1,1-dioxide and 8.8 g of triethylamine in 400 ml of tetrahydrofuran was added. The mixture was stirred at room temperature for 3 hours, cooled to −60°, and a solution of 8.0 g (0.088 mol) of aniline and 11 g of triethylamine in 200 ml of tetrahydrofuran was added. The mixture was stirred at room temperature for 18 hours, refluxed for 3 hours, and part of the tetrahydrofuran was removed by distillation under reduced pressure. The residue was treated with ice water and extracted with dichloromethane. The organic phase was washed with water, dried over sodium sulfate, and evaporated. The residue was redissolved in dichloromethane and ether was added until the solution became turbid. On standing there was collected 22.4 g of a solid precipitate. This was recrystallized from a mixture of 200 ml of tetrahydrofuran and 300 ml of isopropyl ether to give 15.6 g of product, mp 160°–163° dec. Recrystallization from a mixture of 200 ml of dichloromethane and 1600 ml of ether gave 10.4 g of material mp 167°–169° dec.

Anal. Calcd. for C$_{21}$H$_{22}$N$_2$O$_3$S: C, 65.95; H, 5.80; N, 7.32; S, 8.38. Found: C, 65.82; H, 5.85; N, 7.27; S, 8.18.

EXAMPLE 3

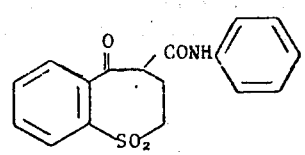

2,3,4,5-Tetrahydro-5-oxo-1-benzothiepin-4-carboxanilide 1,1-Dioxide

A solution of 7.0 g of 2,3-dihydro-5-(1-pyrrolidinyl)-1-benzothiepin-4-carboxanilide and 100 ml of 1N aqueous hydrochloric acid in 200 ml of methanol was refluxed for 1.5 hr. and the methanol was distilled off. The residual mixture was diluted with ice water and the resulting precipitate was collected. It was recrystallized from aqueous methanol to give 4.2 g of product, mp 198°–200° dec. Recrystallization gave an analytical sample, mp 200°–202° dec.

Anal. Calcd. for C$_{17}$H$_{15}$NO$_4$S: C, 61.99; H, 4.59; N, 4.25; S, 9.73. Found: C, 62.20; H, 4.85; N, 4.22; S, 9.51.

EXAMPLE 4

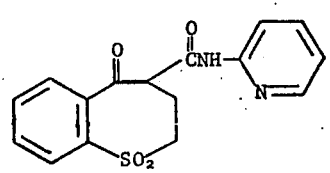

2,3,4,5-Tetrahydro-5-oxo-N(2-pyridyl)-1-benzothiepin-4-carboxamide 1,1-Dioxide

The reaction of 0.1 mol of crude 2,3-dihydro-5-(1-pyrrolidinyl)-1-benzothiepin 1,1-dioxide with phosgene and triethylamine was carried out as described in example 2. The mixture containing the resulting acid chloride was cooled to −50° and a solution of 11.09 g (0.11 mol) of 2-aminopyridine and 13 g (0.15 mol) of triethylamine in 50 ml of tetrahydrofuran was added slowly. The reaction mixture was allowed to slowly warm to room temperature and then stirred for 20 hours. It was decomposed with ice water and extracted with dichloromethane. Evaporation of the dichloromethane gave an oily residue which was heated on a steam bath with a mixture of 200 ml of glacial acetic acid and 100 ml of 1N hydrochloric acid for 45 minutes. The mixture was diluted with ice-water and extracted with dichloromethane. The dichloromethane solution was extracted with 2N sodium hydroxide and the alkaline solution was carefully acidified to pH 5.0 to cause separation of a semi-solid which was repeatedly extracted with dichloromethane (total volume 2000 ml). The dichloromethane layer was washed well with water and dried over sodium sulfate. Evaporation of the solvent gave an oil which was triturated with dichloromethaneether to give 8.5 g of material, mp 105°–115°. Recrystallization from 250 ml of methanol gave 7.3 g of product, mp 168°–171°.

Anal. Calcd. for $C_{16}H_{14}N_2O_4S$: C, 58.17; H, 4.27; N, 8.48; S, 9.71. Found: C, 57.91; H, 4.42; N, 8.56; S, 9.91.

EXAMPLE 5

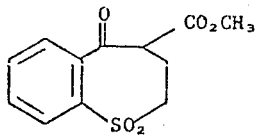

Methyl 2,3,4,5-Tetrahydro-5-oxo-1-benzothiepin-4-carboxylate 1,1-Dioxide.

To a slurry of 0.3 mol of sodium hydride in 200 ml of tetrahydrofuran was added a solution of 21 g (0.1 mol) of 3,4-dihydro-1-benzothiepin-5(2H)-one 1,1-dioxide in 800 ml of tetrahydrofuran. The mixture was stirred at room temperature for 2 hours and a solution of 27 g (0.3 mol) of dimethylcarbonate in 50 ml of tetrahydrofuran was added. It was refluxed under a nitrogen atmosphere for 20 hours, part of the tetrahydrofuran was removed by distillation, the residue was carefully poured into ice water containing excess hydrochloric acid, and the mixture was extracted with dichloromethane. The organic layer was washed with water, dried over sodium sulfate, and evaporated to give 36 g of semi-solid which gave a positive ferric chloride test and an infrared band at 175° cm⁻¹. It was used in subsequent reactions without further purification.

EXAMPLE 6

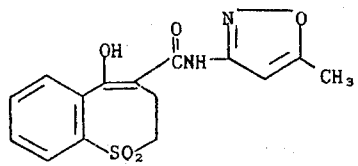

2,3-Dihydro-5-hydroxy-N-(5-methylisoxazol-3-yl)-1-benzothiepin-4-carboxamide 1,1-Dioxide A mixture of 17 g (0.05 mol) of crude methyl 2,3,4,5-tetrahydro-5-oxo-1-benzothiepin-4-carboxylate 1,1-dioxide, 6.0 g (0.061 mol) of 3-amino-5-methylisoxazole, and 350 ml of toluene was refluxed for 24 hours in a Soxhlet apparatus the thimble of which contained 20 g of Linde type 4A molecular sieve. The mixture was diluted with 500 ml of ether and the resulting precipitate (10 g) was collected and recrystallized from 400 ml of tetrahydrofuran to give 9.0 g of product mp 226°–228°. Recrystallization gave an analytical sample mp 227°–229°.

Anal. Calcd. for $C_{15}H_{12}N_2O_5S$: C, 53.88; H, 4.22; N, 8.38; S, 9.59. Found: C, 54.17; H, 4.36; N, 8.34; S, 9.81.

EXAMPLE 7

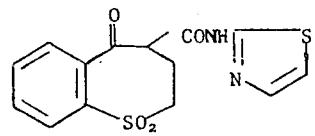

2,3,4,5-Tetrahydro-5-oxo-N-(2-thiazolyl)-1-benzothiepin-4-carboxamide 1,1-Dioxide This compound was prepared from crude 2,3,4,5-tetrahydro-5-oxo-1-benzothiepin-4-carboxylate 1,1-dioxide and 2-aminothiazole using the same procedure described in the preceding example. The crude precipitate (10.5 g) contained a difficultly removable polymeric impurity which could be detected by the presence of an infrared band at 1750 cm⁻¹. It was purified as follows: The precipitate was dissolved in 300 ml of tetrahydrofuran and 700 ml of ether was added. A polymeric material which initially separated out was filtered off and the filtrate was allowed to stand at room temperature, whereupon 4.5 g of material mp 239°–245° dec crystallized out. This process was repeated and the resulting crystalline product (2.7 g) was recrystallized from 250 ml of methanol to give 2.0 g of product whose infrared spectrum showed no band at 1750 cm⁻¹.

Anal. Calcd. for $C_{14}H_{12}N_2O_4S_2$: C, 49.99; H, 3.60; N, 8.33; S, 19.06. Found: C, 49.95; H, 3.73; N, 8.24; S, 18.93.

We claim:
1. A compound of the formula

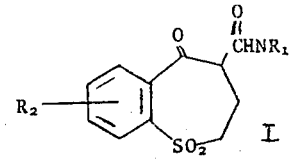

wherein $R_1$ is aryl of 6–10 carbon atoms, pyridyl, or thiazole and $R_2$ is hydrogen, lower alkyl, halogen, lower alkoxy or trifluoromethyl and the corresponding alkali metal salts.

2. A compound according to claim 1 which is 2,3,4,5-tetrahydro-5-oxo-1-benzothiepin-4-carboxanilide 1,1-dioxide.

3. A compound according to claim 1 which is 2,3,4,5-tetrahydro-5-oxo-N(2-pyridyl)-1-benzothiepin-4-carboxamide 1,1-dioxide.

4. A compound according to claim 1 which is 2,3,4,5-tetrahydro-5-oxo-N-(2-thiazolyl)-1-benzothiepin-4-carboxamide 1,1-dioxide.

* * * * *